(12) United States Patent
Bernhardt

(10) Patent No.: US 8,537,970 B2
(45) Date of Patent: Sep. 17, 2013

(54) X-RAY RADIATOR TO GENERATE QUASI-MONOCHROMATIC X-RAY RADIATION, AND RADIOGRAPHY X-RAY ACQUISITION SYSTEM EMPLOYING SAME

(75) Inventor: Philipp Bernhardt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 196 days.

(21) Appl. No.: 13/154,746

(22) Filed: Jun. 7, 2011

(65) Prior Publication Data

US 2011/0299658 A1 Dec. 8, 2011

(30) Foreign Application Priority Data

Jun. 7, 2010 (DE) .................... 10 2010 022 851

(51) Int. Cl.
*G21K 1/06* (2006.01)
(52) U.S. Cl.
USPC ............................................. 378/84; 378/70
(58) Field of Classification Search
USPC ................. 378/84, 85, 70, 71, 82, 83
See application file for complete search history.

(56) References Cited

U.S. PATENT DOCUMENTS

| | | | |
|---|---|---|---|
| 5,082,621 A | 1/1992 | Wood | |
| 5,757,882 A * | 5/1998 | Gutman | ........................... 378/84 |
| 6,521,101 B1 | 2/2003 | Skulina et al. | |
| 6,863,409 B2 | 3/2005 | Cho et al. | |
| 2007/0030947 A1 | 2/2007 | Popescu | |

OTHER PUBLICATIONS

"Laterally-Graded SiGe Crystals for High Resolution Synchrotron Optics," Erko et al., Cryst. Res. Technol. vol. 37, No. 7 (2002) pp. 685-704.
"Design and Optimization of Multilayer Coatings for Hard X-ray Mirrors," Ivan et al., Proceedings of SPIE, vol. 3773 (1999), pp. 107-112.

* cited by examiner

*Primary Examiner* — Hoon Song
(74) *Attorney, Agent, or Firm* — Schiff Hardin LLP

(57) ABSTRACT

For a quasi-monochromatic x-ray radiation with high radiation intensity, an x-ray radiator generates quasi-monochromatic x-ray radiation to expose a subject from a point-shaped radiation source that emits a polychromatic x-ray radiation, and having a diffraction device to diffract the polychromatic x-ray radiation. The diffraction device has a super-mirror made of crystalline material with a flat surface. In the super-mirror, the crystalline material has at least one (in particular continuous) variation of the lattice plane spacing of the crystal lattice. The radiation source and the diffraction device are arranged such that quasi-monochromatic x-ray radiation is generated from the polychromatic x-ray radiation by partial reflection at the super-mirror.

15 Claims, 5 Drawing Sheets

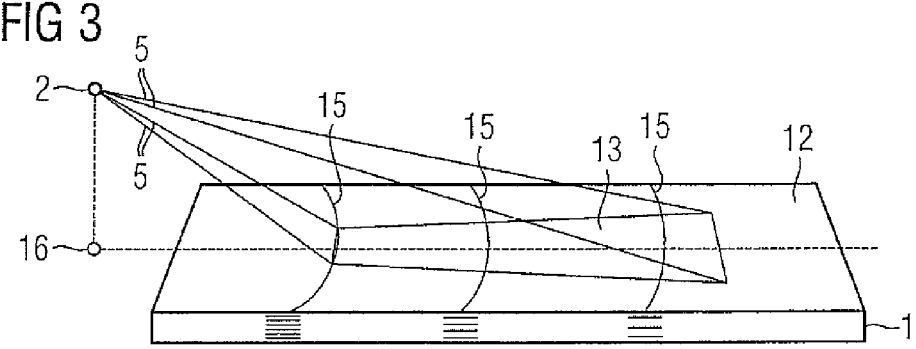
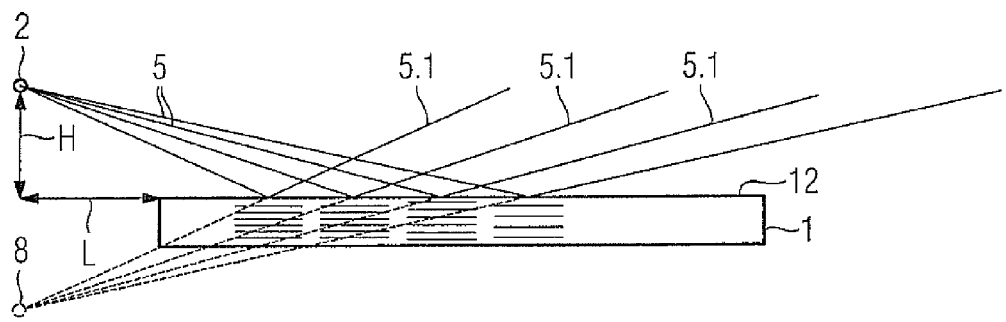
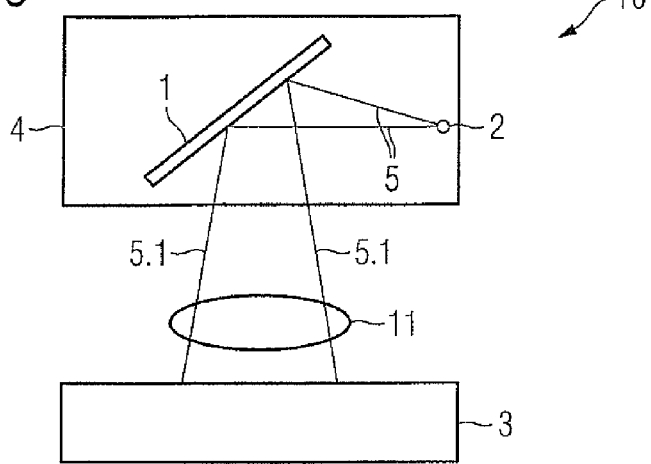

FIG 6
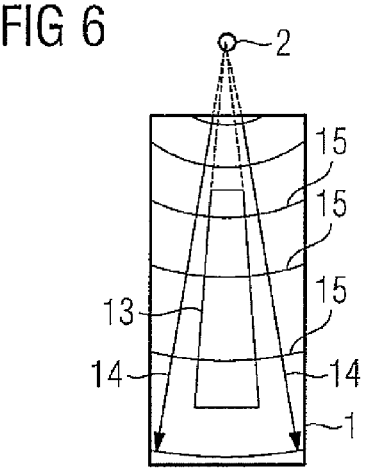
FIG 7
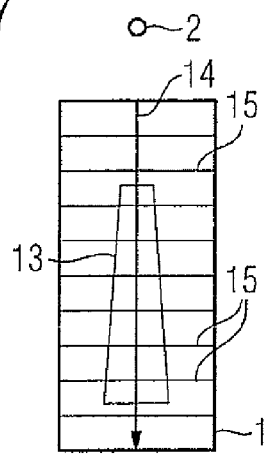

Displacement Unit

X-RAY RADIATOR TO GENERATE QUASI-MONOCHROMATIC X-RAY RADIATION, AND RADIOGRAPHY X-RAY ACQUISITION SYSTEM EMPLOYING SAME

BACKGROUND OF THE INVENTION

1. Field of the Invention

The present invention concerns an x-ray radiator to generate quasi-monochromatic x-ray radiation, and a medical radiography x-ray acquisition system embodying such an x-ray 2. Description of the Prior Art X-ray systems for x-ray-based medical imaging are known with the following design. A point-shaped x-ray source (bremsstrahlung generated by an x-ray beam at an anode) in an x-ray radiator emits polychromatic x-ray radiation. The radiation can be brought into the shape of a delimited fan by a collimator. The x-ray radiation penetrates a subject to be exposed, in which the radiation is attenuated before it is received by an image receiver with spatial resolution. In the use of such x-ray systems, a significant efficiency loss occurs due to the polychromatic braking spectrum. It is known that for each task, i.e. the imaging of a specific subject within a defined background and a given geometry—there is precisely one quantum energy that represents the optimal compromise between patient dose, contrast and noise, and therefore has the highest efficiency. A polychromatic spectrum therefore inevitably contains spectrum portions that are superfluous or disruptive for the task at hand. Since energies adjacent to the optimal quantum energy likewise have a very high efficiency, to satisfy the object of a good image quality it is sufficient to use a somewhat more broadly spread quantum energy (quasi-monochromatic), for example limited to a range of approximately 15 keV. In comparison, a perfectly monochromatic x-ray radiation insignificantly increases the efficiency.

A tunable, quasi-monochromatic, efficient x-ray radiator is a requirement for an ideal x-ray system, however, the production of a quasi-monochromatic x-ray beam from the polychromatic spectrum is complicated. A common method to achieve this approximately is the diffraction of the polychromatic x-ray radiation (generated with the use of known x-ray sources) by the Bragg diffractions (see FIG. 2) at crystals. However, such methods always contain a very large radiation intensity loss both spectrally and spatially. For this reason such x-ray radiators according to the prior art have generally not been used in the radioscopy of large and thick tissue slices, or only what are known as scan exposures are implemented.

SUMMARY OF THE INVENTION

An object of the present invention is to provide an x-ray radiator that ensures the generation of optimally quasi-monochromatic x-ray radiation with a high radiation intensity and an optimally large exposure area, The above object is achieved in accordance with the present invention by an x-ray radiator that generates quasi-monochromatic radiation in order to irradiate a subject, the x-ray radiator having a punctiform radiation source that emits polychromatic x-ray radiation, a diffraction device that diffracts the polychromatic x-ray radiation, the diffraction device having a super-mirror composed of crystalline material with a flat surface, and the crystalline material having at least one continuous variation of the lattice plane spacing of its crystal lattice, and the radiation source and the diffraction device are arranged with respect to each other to cause quasi-monochromatic x-ray radiation to be generated from a portion of the polychromatic x-ray radiation by Bragg reflection at said super-mirror.

By means of the x-ray radiator according to the invention, polychromatic x-ray radiation is converted into quasi-monochromatic x-ray radiation by diffraction at a super-mirror with a continuous variation (grading) of the lattice plane spacing of the crystal lattice by reflection below the Bragg condition.

The crystalline material has a variation of the lattice plane spacing perpendicular to the surface. Due to this variation, known as a "local" variation, the Bragg peak is expanded and quasi-monochromatic x-ray radiation is generated. In the quasi-monochromatic x-ray radiation that is generated in this manner, the radiation intensity is markedly higher than in x-ray radiation converted into quasi-monochromatic x-ray radiation using a known filter. Quasi-monochromatic x-ray radiation means radiation with an energy band of up to approximately 15 keV. With the x-ray radiator of the invention, in x-ray imaging the result or the image quality per patient dose that is used can be markedly increased (for example by approximately a factor of 3 in radiography). Relatively little x-ray intensity is lost due to the x-ray radiator according to the invention, such that a full image x-ray imaging (in contrast to a scan imaging in which a very narrow x-ray beam is moved across a subject) can be implemented with good image quality. Moreover, the ability to activate the quantum energy as needed allows an adaptation of the exposure parameters to the patient thickness ("automatic exposure regulation"). Overall, in accordance with the invention the image quality in x-ray imaging is increased so that making a diagnosis is simpler and safer, or alternatively the dose can be reduced while maintaining image quality. For example, the variation of the lattice plane spacing perpendicular to the surface has a Gaussian distribution around a mean, such that an energy band of up to 15 keV can be generated. A linear or other continuous distribution of the variation can also be provided. For example, the crystalline material can be formed by an artificially generated crystal.

In an embodiment of the invention, a particularly constant energy selection can be generated when the crystalline material has a continuous variation of the lattice plane spacing in at least one direction along the surface.

According to a further embodiment of the invention, the reflected part of the polychromatic x-ray radiation has quantum energies that have at least 40 keV and at most 90 keV, in particular 50 to 70 keV. This range is particularly suitable for x-ray imaging in radiography, such as for individual exposures of body parts and organs. For example, the energy band selected from this range extends beyond 15 keV, thus for example from 50 keV to 65 keV.

According to a further embodiment of the invention, the (in particular continuous) variation of the lattice plane spacing of the crystal lattice along the surface is such that the super-mirror has circular arc-shaped contour lines (isolines) of the lattice plane spacing (with a common center) on its surface. A super-mirror fashioned in such a manner enables a particularly uniform reflection of energy bands given suitable positioning, and therefore enables a generation of quasi-monochromatic x-ray radiation. For example, the surface of such a super-mirror can be fashioned in the shape of a rectangle, wherein the contour lines can run perpendicular to the longitudinal direction of the super-mirror.

For a particularly simple production of the super-mirror with a nevertheless effective applicability for the generation of quasi-monochromatic x-ray radiation, the (in particular continuous) variation of the lattice plane spacing of the crystal lattice along the surface is advantageously such that the super-mirror has, on its surface, straight contour lines of the lattice plane spacing that are parallel to one another. The surface of such a super-mirror can likewise be fashioned in the shape of a rectangle, for example, wherein the contour lines can run perpendicularly to the longitudinal direction of the super-mirror.

According to a further embodiment of the invention, the super-mirror is arranged in relation to the radiation source such that the contour lines are perpendicular to the projection of the central ray of the x-ray radiation on the super-mirror. This is advantageous both for a super-mirror with one-dimensionally varied lattice plane spacing and two-dimensionally varied lattice plane spacing. Given such a positioning of the x-ray source, a particularly effective reflection of the x-ray radiation is ensured so that quasi-monochromatic x-ray radiation of high intensity can be generated. If, as described above, the super-mirror is rectangular and the contour lines are perpendicular to the longitudinal direction, it is advantageous for the projection of the central ray of the x-ray radiation to be parallel to the longitudinal direction.

According to a further embodiment of the invention, the super-mirror is arranged such that it can be displaced in a direction perpendicular to its surface. in this way different energy bands can be selectively reflected with one and the same super-mirror. Different applications in x-ray imaging are thus possible.

The super-mirror is advantageously formed from a combination of the materials nickel and carbon, or from a combination of the materials molybdenum and silicon, or from a combination of the materials tungsten and silicon.

According to a further embodiment of the invention, the crystal lattice has lattice plane spacings that amount to at least 0.02 nm and at most 0.25 nm. In this way quantum energies or energy bands between 40 keV and 90 keV can be reflected as needed.

An additional portion of the polychromatic x-ray radiation, namely the portion that is not reflected by means of Bragg reflection, is transmitted or absorbed. In order to prevent x-ray radiation from damaging devices or people located outside of the x-ray radiator, the super-mirror is coated or covered on its back side with a highly absorbent material (such as lead). In this way the entirety of the non-reflected x-ray radiation is absorbed. Tungsten or molybdenum can be used as an alternative to lead, for example.

The invention also concerns a medical radiography x-ray acquisition system with an x-ray radiator to generate quasi-monochromatic x-ray radiation as described above, and an x-ray detector.

As used herein, a "continuous variation" mean a varying function that satisfies the mathematical continuity criteria and does not have any jumps. The variation can be linear or exponential, for example.

BRIEF DESCRIPTION OF THE DRAWINGS

FIG. 3 is a perspective view of an x-ray beam striking a super-mirror with two-dimensional variation of a lattice plane spacing.

FIG. 4 is a section through a super-mirror with two-dimensional variation of the lattice plane spacing.

FIG. 5 is a view of a medical x-ray acquisition system according to the invention.

FIG. 6 is a view of a super-mirror with two-dimensional variation of the lattice plane spacing.

FIG. 7 is a view of a super-mirror with one-dimensional variation of the lattice plane spacing.

DESCRIPTION OF THE PREFERRED EMBODIMENTS

Figure 1:
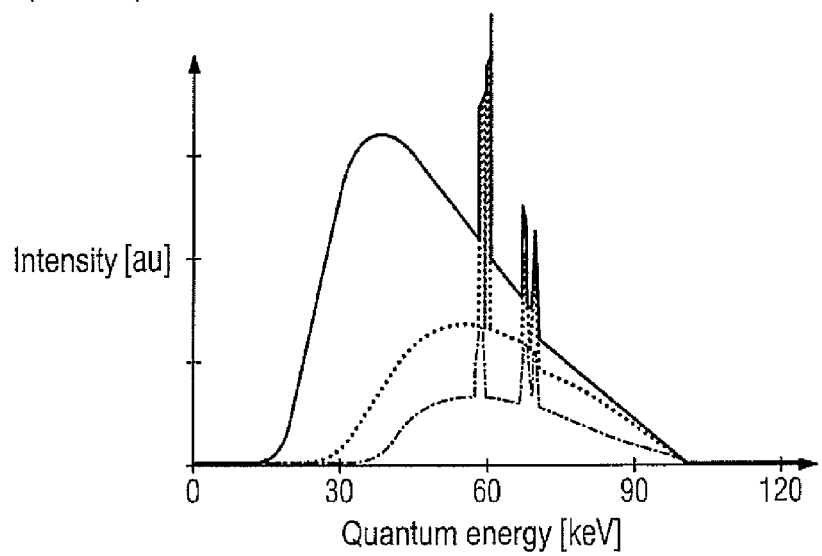
FIG. 1 shows the quantum energy of a known x-ray source, with and without a filter.

FIG. 1 shows an x-ray braking spectrum of a conventional, polychromatic x-ray source according to the prior art, wherein the solid line shows an unfiltered x-ray spectrum and the dashed line and dash-dot line show an x-ray spectrum filtered with a copper filter. All x-ray spectra are generated with comparable tube voltage of the x-ray source of approximately 100 kV. The dash-dot x-ray spectrum was generated with a stronger filtering than the dashed curve. Low-energy portions of the x-ray spectrum are masked out via the use of a filter; however, the intensity is also severely reduced. Given the generation of a quasi-monochromatic x-ray radiation— thus an x-ray radiation whose quantum energy is limited to an energy band of essentially 15 keV or less—so little intensity remains that an imaging with full image acquisition is still possible only for very thin objects. The highest energy of the x-ray spectrum is determined by the tube voltage.

Figure 2:
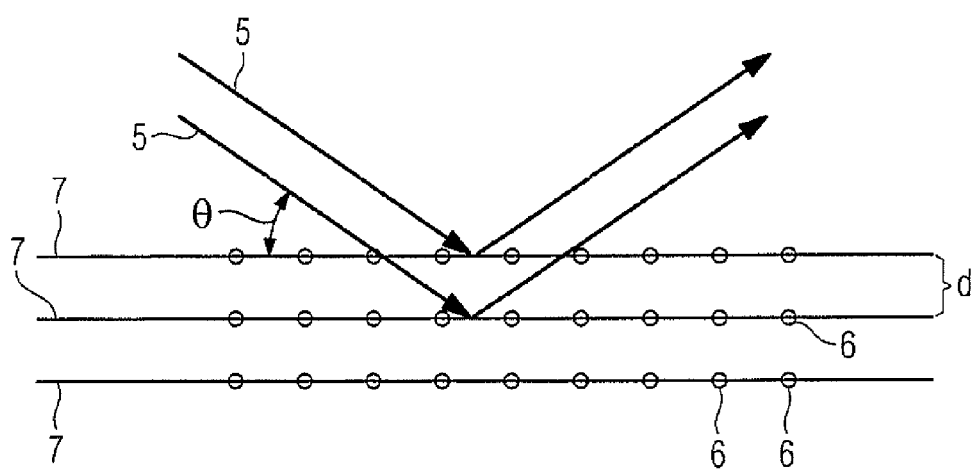
FIG. 2 shows the reflection of x-ray radiation at a lattice under the Bragg condition according to the prior art.

The Bragg reflection of x-ray radiation is shown in FIG. 2. The atoms 6 of a crystalline material are arranged in lattice planes 7 with a lattice plane spacing d that is generally regularly fixed. X-ray radiation 5 that is incident with an angle of incidence $\theta$ is then reflected precisely when the wavelength $\lambda$ of the x-ray radiation 5 satisfies the following condition: $n\lambda = 2d \sin \theta$, wherein n is an arbitrary whole number. All other wavelengths are transmitted or absorbed.

The invention utilizes the Bragg reflection to generate quasi-monochromatic x-ray radiation from polychromatic x-ray radiation by means of a reflector with a flat surface, which reflector has a continuous variation of the lattice plane spacing of the crystal lattice perpendicular to the surface ("local") and simultaneously along the surface. The reflector can be of the type known as a multilayered super-mirror. Due to the continuous variation (grading) of the lattice plane spacing d perpendicular to the surface, by means of the Bragg reflection not only a single wavelength but rather a whole range (an energy band) is reflected, corresponding to the respective lattice plane spacing at which the respective x-ray strikes. Due to the variation along the surface, given the point-shaped x-ray source and the flat surface of the super-mirror a constant reflected energy band is ensured given angles of incidence of the x-ray radiation that vary along the surface. The variation of the lattice plane spacing perpendicular to the surface is, for example, such that an energy band of up to 15 keV of the x-ray radiation is reflected. The variation can have a Gaussian distribution around a mean, for example, wherein the mean corresponds to a reflected energy of 50 keV or 70 keV, for example. The "local" variation (perpendicular to the surface) is known from the prior art, for example in the construction of telescopes.

As is shown in FIG. 3, the lattice plane spacings vary along the surface 12 of the super-mirror 1 in addition to the variation (not shown) perpendicular to the surface. The surface 12 of the super-mirror 1 is fashioned as a rectangle, for example, with a longitudinal direction and a transversal direction. The variation of the lattice plane spacing along the surface is thereby continuously developed such that contour lines 15 (thus lines with the same lattice plane spacing) in the shape of circular arcs are present on the surface 12. According to one alternative, the contour lines 15 can be formed as sections of circular lines, for example, with a common center situated in the plane of the surface of the super-mirror. This center can, for example, be placed outside or at a first end of the super-mirror in the longitudinal direction. In this case the x-ray source of the x-ray radiator is preferably in such a position in a plane above the super-mirror that a perpendicular projection on the plane of the surface of the super-mirror falls precisely at the center of the circular lines. However, deviations from this geometry are also possible.

The x-ray fan formed from the x-ray radiation emitted by the x-ray source 2 has an incident area 13 on the super-mirror. The incident area 13 strikes at a different (in particular smaller) lattice plane spacing at its first end situated closer to the x-ray source than at its second end situated further from the x-ray source. In particular, the lattice plane spacing varies continuously toward larger lattice plane spacings along the incident area from the first end to the second end. The variation (not shown) of the lattice plane spacings perpendicular to the surface generates the quasi-monochromatic energy bands expands the Bragg peak (see FIG. 9), while the variation along the surface ensures that the same energy band is always preserved. The surface of the super-mirror 1 is shown in overview in FIG. 6, wherein the direction 14 of the continuous variation runs radially starting from the center 16 formed by the projection of the x-ray source 2 on the plane of the super-mirror 1.

A longitudinal section through the super-mirror 1 of FIG. 3, from the first end to the second end (indicated with dashed line in FIG. 3), is shown in FIG. 4, wherein it is also shown that different x-rays strike at different points on the surface 12 (and therefore at different lattice plane spacings). The reflected x-ray radiation 5.1 runs in the manner as if the x-ray radiation emanated from a virtual radiation source 8 created by mirroring the x-ray source 2 at the surface 12. A height interval H and a length interval L exist between the x-ray source 2 and the plane of the surface 12. The variation of the lattice plane spacings that is present perpendicular to the surface is again not shown.

An additional embodiment of the invention is shown in FIG. 7. For a simplified production of the super-mirror 1, the continuous variation of the lattice plane spacing along the surface is fashioned—in the direction 14 from the first end situated closer to the x-ray source to its second end situated further from the x-ray source—such that the contour lines 15 are straight and fashioned in parallel in this case.

Figure 9:
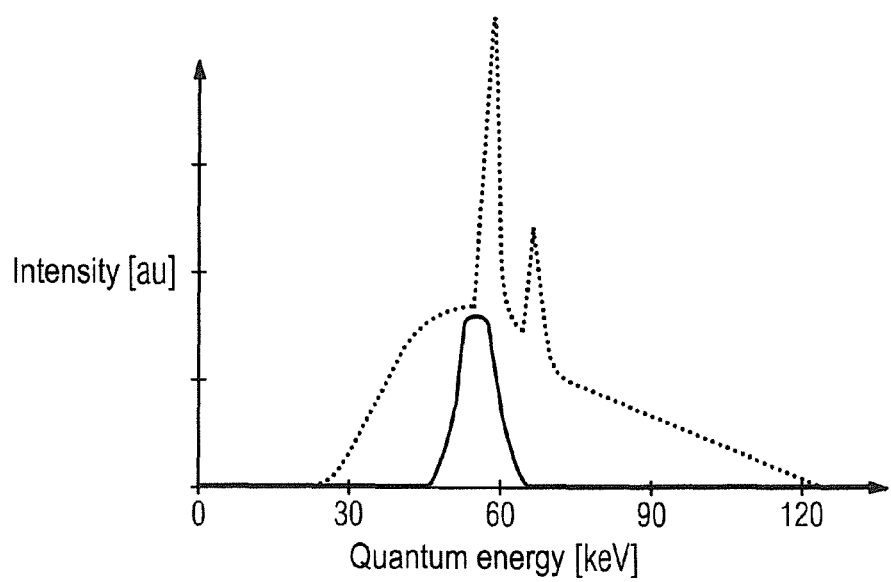
FIG. 9 is a view of the quantum energy of a known x-ray source in comparison to the x-ray radiator according to the invention.

In FIG. 9 it is shown in the solid curve how an x-ray spectrum of an x-ray radiator can appear with duplicate variation according to the invention. In comparison to this, the x-ray spectrum of a conventional x-ray radiation filtered with a copper filter is shown in a dashed line. The x-ray spectrum generated with the x-ray radiator according to the invention is quasi-monochromatic and shows a pronounced maximum with low intensity loss across a limited quantum energy band of, for example, 10 to 15 keV; the remaining energies have virtually no intensity. Full-field x-ray exposures with a good achievable quality can be implemented with one x-ray shot (one-time exposure) by means of such a quasi-monochromatic x-ray spectrum.

A radiography x-ray acquisition system 10 which has an x-ray radiator according to the invention with a polychromatic radiation source 2 and a super-mirror 1 is shown as an example in FIG. 5. The reflected x-ray radiation 5.1 irradiates a subject 11 and subsequently strikes an x-ray detector 3. The x-ray radiator can be installed permanently or so as to be movable. For example, it can be arranged together with the x-ray detector at a mount, for example in the form of a C-arm. Additional arrangements (for example with a mobile x-ray detector) are likewise possible.

Figure 8:
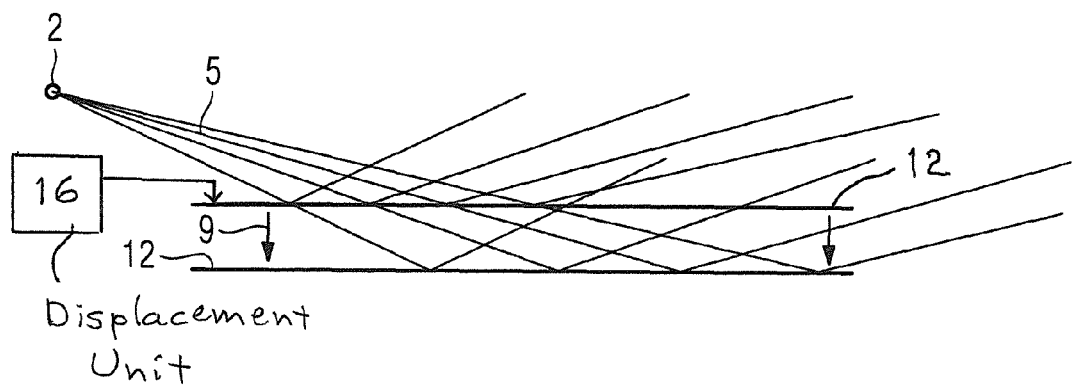
FIG. 8 is a side view of the surface of a super-mirror with incident x-rays in two positions perpendicular to the surface.

During the acquisition of an x-ray image, the arrangement between polychromatic radiation source 2 and super-mirror is not moved. However, a displacement can by all means be provided between two exposures. According to one embodiment of the invention, the super-mirror is arranged such that it can be displaced perpendicular to the crystal surface. Such a displacement leads to a variation of the selected quasi-monochromatic energy band, such that respective different energy bands can be selected by means of such a displaceable x-ray radiator, even without exchanging the super-mirror. Such a displacement 9 and its effect on the position of the incident x-ray radiation 5, and therefore on the position of the incident surface, is shown in FIG. 8. Due to the displacement of the incident area, the x-ray radiation strikes a different lattice plane spacing; a different energy band is also thereby reflected. A displacement device 16 can be provided, such that a displacement (for example by means of a motor) can be activated automatically.

For example, the super-mirror can be formed from a combination of the materials nickel and carbon or from a combination of the materials molybdenum and silicon, or from a combination of the materials tungsten and silicon. These materials can be applied in a simple manner with varying lattice plane spacings, for example can be deposited or coated. In order to generate such lattice plane spacings, artificial crystal structures are generated, for example. An example of the production of such slices is known from the document "Design and optimization of multilayer coatings for hard x-ray mirrors" by A. Ivan et al., Proceedings of SPIE, Vol. 3773, 1999, Denver Colo., Pages 107 and the following.

An embodiment of the lattice plane spacing of the crystal lattice between at least 0.02 nm and at least 0.25 nm is particularly advantageous since quantum energies between 40 keV and 90 keV can be reflected in this way.

The super-mirror can be coated or covered with lead (for example) on its back side. In this way the unreflected x-ray radiation is absorbed and cannot propagate further on the back side of the super-mirror and there cause damage to devices or people.

According to a further embodiment of the invention, with a higher tube voltage (in comparison to normal tube voltages of approximately 50 keV to 100 keV) of over 100 keV (for example 125 keV or 150 keV; "high voltage tubes") the quantum number of specific energies can be increased since the efficiency of the x-ray radiator is improved. However, the disadvantage of this increase lies in that quanta of a higher order (two/three . . . times the energy; for example at 50 keV, also 100 keV and 150 keV) are also reflected due to the periodicity of the Bragg equation.

Figure 10:
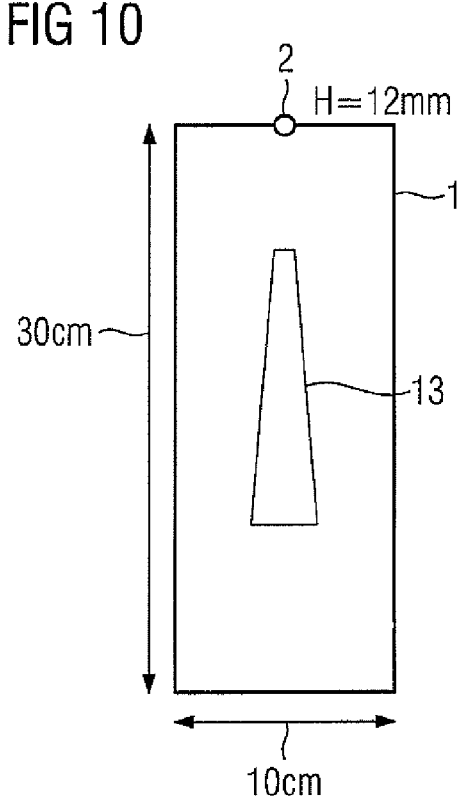
FIG. 10 shows a first exemplary arrangement of a super-mirror.
Figure 11:
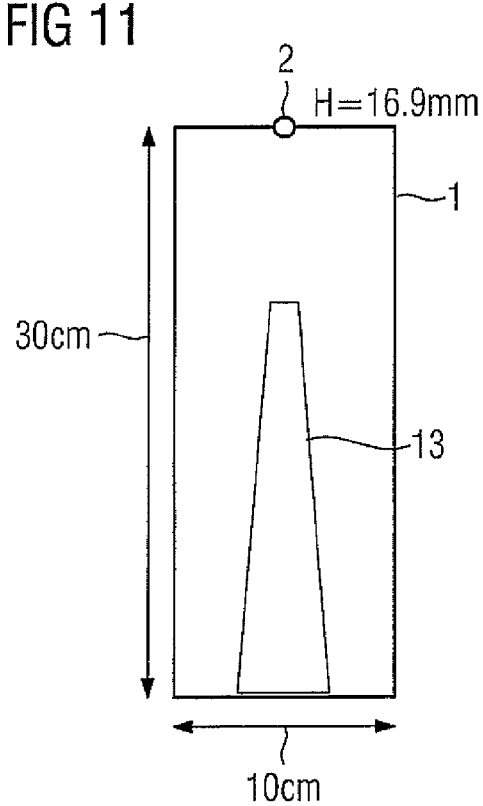
FIG. 11 shows an additional exemplary arrangement of a super-mirror.

In an example of an x-ray radiator, the super-mirror can be 30 cm long and 10 cm wide and have a lattice plane spacing between 0.05 nm and 0.22 nm. Given an aperture angle of the x-ray beam of 7° in both respective directions and a height interval of the x-ray source from surface of the super-mirror of H=12 mm as well as a length interval L=0, the incident area is formed as shown in FIG. 10; given a height interval H=16.9 mm the height interval is formed as shown in FIG. 11.

With the use of the x-ray radiator according to the invention, the perfusion, i.e. the image quality per patient dose used (x-ray dose per patient), can be markedly increased (by up to a factor of 3 in radiography). Little x-ray intensity is lost due to the invention. It is not necessary to implement x-ray acquisitions per scan methods in order to still obtain sufficient intensity, as in devices according to the prior art. Moreover, the ability to activate the energy allows a (presently typical) adaptation of the exposure parameters to the patient thickness ("automatic exposure regulation").

The invention can be briefly summarized as follows. For a quasi-monochromatic x-ray radiation with high radiation intensity, an x-ray radiator is provided to generate quasi-monochromatic x-ray radiation to expose a subject. The x-ray radiator has a point-shaped radiation source to emit a polychromatic x-ray radiation and a diffraction device to diffract the polychromatic x-ray radiation. The diffraction device has a super-mirror made of crystalline material with a flat surface, in which super-mirror the crystalline material has at least one (in particular continuous) variation of the lattice plane spacing of the crystal lattice. The radiation source and the diffraction device are arranged such that quasi-monochromatic x-ray radiation is generated from the polychromatic x-ray radiation by partial reflection at the super-mirror. Both a continuous variation of the lattice plane spacing in at least one direction along the surface, and a variation of the lattice plane spacing perpendicular to the surface, are preferably provided.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray radiation device to generate quasi-monochromatic x-ray radiation, comprising:
    a punctiform radiation source that emits polychromatic x-ray radiation;
    a diffraction device on which said polychromatic x-ray radiation is incident, said diffraction device diffracting the polychromatic x-ray radiation incident thereon and having a super-mirror comprised of crystalline material having a flat surface, said crystalline material in said super-mirror having a crystal lattice exhibiting a lattice plane spacing that continuously varies within said crystal lattice;
    said diffraction device causing quasi-monochromatic x-ray radiation to be generated from a portion of the polychromatic x-ray radiation incident thereon by Bragg reflection at said super-mirror; and
    a displacement device that displaces said super-mirror in a displacement direction perpendicular to said flat surface, the displacement of said super-mirror in said direction perpendicular to said flat surface changing an energy band in which said quasi-monochromatic x-ray radiation is generated, and thereby allowing selection of said energy band dependent on said displacement.

2. An x-ray radiation device as claimed in claim 1 wherein said lattice plane spacing continuously varies along at least one direction of said flat surface.

3. An x-ray radiation device as claimed in claim 1 wherein said crystalline material has a continuously varying lattice plane spacing in a direction perpendicular to said flat surface.

4. An x-ray radiation device as claimed in claim 1 wherein said polychromatic x-ray radiation incident on said diffraction device, other than said portion reflected at said super-mirror, is transmitted through or absorbed by said diffraction device.

5. An x-ray radiation device as claimed in claim 1 wherein said diffraction device causes generation of said quasi-monochromatic x-ray radiation with a quantum energy between 40 keV and 90 keV.

6. An x-ray radiation device as claimed in claim 1 wherein said crystalline material has a continuously varying lattice plane spacing in at least one direction along said flat surface that gives said super-mirror straight contour lines of said lattice plane spacing on said flat surface.

7. An x-ray radiation device as claimed in claim 6 wherein said straight contour lines are parallel to each other.

8. An x-ray radiation device as claimed in claim 6 wherein said polychromatic x-ray radiation emitted by said radiation source contains a central ray, and wherein said super-mirror is oriented with respect to said radiation source to cause said contour lines to be parallel to a projection of said central ray of the x-ray radiation on the super-mirror.

9. An x-ray radiation device as claimed in claim 1 wherein said crystalline material has said continuously varying lattice plane spacing in at least one direction along said flat surface that gives said super-mirror arcuate contour lines of said lattice plane spacing on said flat surface.

10. An x-ray radiation device as claimed in claim 9 wherein said polychromatic x-ray radiation emitted by said radiation source contains a central ray, and wherein said super-mirror is oriented with respect to said radiation source to cause said contour lines to be parallel to a projection of said central ray of the x-ray radiation on the super-mirror.

11. An x-ray radiation device as claimed in claim 1 wherein said super-mirror is comprised of a combination of materials selected from the group consisting of a combination of nickel and carbon, a combination of molybdenum and silicon, and a combination of tungsten and silicon.

12. An x-ray radiation device as claimed in claim 1 wherein said lattice plane spacing of said crystal lattice of said crystalline material is in a range between 0.02 nm and 0.25 nm.

13. An x-ray radiation device as claimed in claim 1 wherein said super-mirror has a front side on which said polychromatic radiation is incident and a rear side opposite to said front side, and wherein said rear side of said super-mirror comprises a coating of a material that absorbs said polychromatic radiation.

14. An x-ray radiation device as claimed in claim 13 wherein said material is lead.

15. A medical radiography x-ray acquisition system comprising:
    an x-ray radiation device comprising a punctiform radiation source that emits polychromatic x-ray radiation, a diffraction device on which said polychromatic x-ray radiation is incident, said diffraction device diffracting the polychromatic x-ray radiation incident thereon and having a super-mirror comprised of crystalline material having a flat surface, said crystalline material in said super-mirror having a crystal lattice exhibiting a lattice plane spacing that continuously varies within said crystal lattice, and said diffraction device causing quasi-monochromatic x-ray radiation to be generated from a portion of the polychromatic x-ray radiation incident thereon by Bragg reflection at said super-mirror;
    a displacement device that displaces said super-mirror in a displacement direction perpendicular to said flat surface, the displacement of said super-mirror in said direction perpendicular to said flat surface changing an energy band in which said quasi-monochromatic x-ray radiation is generated, and thereby allowing selection of said energy band dependent on said displacement; and an x-ray detector located in a path of said quasi-monochromatic x-ray radiation, said x-ray radiation device and said x-ray detector being adapted to receive an examination subject therebetween that is also irradiated by said quasi-monochromatic x-ray radiation, and said x-ray detector generating electrical signals representing said quasi-monochromatic x-ray radiation, in said band, attenuated by the examination subject, in a form allowing generation of an x-ray image of the examination subject therefrom.

* * * * *